(12) United States Patent
Blackwell

(10) Patent No.: US 9,650,284 B2
(45) Date of Patent: *May 16, 2017

(54) DENTAL GLASS COMPOSITION

(75) Inventor: Gordon Blackwell, Constance (DE)

(73) Assignee: Dentsply International Inc., York, PA (US)

( * ) Notice: Subject to any disclaimer, the term of this patent is extended or adjusted under 35 U.S.C. 154(b) by 629 days.

This patent is subject to a terminal disclaimer.

(21) Appl. No.: 11/719,150

(22) PCT Filed: Oct. 28, 2005

(86) PCT No.: PCT/EP2005/011584
§ 371 (c)(1),
(2), (4) Date: Oct. 7, 2009

(87) PCT Pub. No.: WO2006/050829
PCT Pub. Date: May 18, 2006

(65) Prior Publication Data
US 2010/0152318 A1 Jun. 17, 2010

(30) Foreign Application Priority Data
Nov. 12, 2004 (EP) .................... 04027012

(51) Int. Cl.
 *A61K 6/08* (2006.01)
 *C03C 3/062* (2006.01)
 *A61K 6/083* (2006.01)
(52) U.S. Cl.
 CPC ............ *C03C 3/062* (2013.01); *A61K 6/0835* (2013.01)

(58) Field of Classification Search
 USPC ....... 523/116; 433/228.1; 501/73, 151, 5, 76
 See application file for complete search history.

(56) References Cited

U.S. PATENT DOCUMENTS

| | | | | |
|---|---|---|---|---|
| 4,055,703 A | * | 10/1977 | Rinehart | 428/410 |
| 4,861,808 A | * | 8/1989 | Billington et al. | 523/116 |
| 4,900,697 A | * | 2/1990 | Akahane et al. | 501/57 |
| 5,215,459 A | * | 6/1993 | Ney et al. | 433/215 |
| 5,520,725 A | * | 5/1996 | Kato et al. | 106/35 |
| 6,107,229 A | * | 8/2000 | Luck et al. | 501/151 |
| 6,297,181 B1 | * | 10/2001 | Kunert et al. | 501/57 |
| 6,869,984 B2 | * | 3/2005 | Kawashima et al. | 523/116 |
| 2005/0142077 A1 | * | 6/2005 | Zimmer et al. | 424/57 |

FOREIGN PATENT DOCUMENTS

EP 1190994 A1 * 3/2002

* cited by examiner

*Primary Examiner* — Tae H Yoon
(74) *Attorney, Agent, or Firm* — McNees Wallace & Nurick LLC

(57) ABSTRACT

An aluminosilicate glass composition comprising: (a) 10-35% by weight of silica; (b) 10-35% by weight of alumina; (c) 3-30% by weight of zinc oxide; (d) 4-30% by weight $P_2O_5$; and (e) 3-25% by weight of fluoride which contains at most 3% by weight of alkaline metals calculated as $M_2O$, wherein M is Li, Na, and/or K, and wherein the weight ratio of the sum of zinc oxide and fluoride to $P_2O_5$ of from 0.8 to 3.0.

18 Claims, No Drawings

DENTAL GLASS COMPOSITION

FIELD OF THE INVENTION

The present invention relates to an aluminosilicate glass composition and a particulate dental filler characterized by the glass composition of the invention. Moreover, the present invention relates to a dental restorative composition comprising the particulate glass filler of the invention and a process for the preparation of a dental cement composition. Finally, the present invention relates to the use of the glass composition of the invention for the preparation of a dental restorative composition.

BACKGROUND TO THE INVENTION

EP-A 0 997 132 discloses dental glasses useful as fillers for a light curable dental composite. There is no evidence disclosed by EP-A 0 997 132 that the glasses disclosed therein are reactive and useful in a dental cement.

EP-A 0 469 573 discloses a glass ionomer cement containing a reactive glass filler and a water-insoluble heavy metal salt. The glass composition according to EP-A 0 469 573 does not contain zinc as an essential component.

U.S. Pat. No. 4,775,592 discloses a fluoroaluminosilicate glass powder for a dental glass ionomer cement, a surface of which is treated with a fluoride in a specific amount in order to improve the crushing strength and the fluidity of the cement.

Glasses form an important part of many dental restorative materials, and are used in dentistry in many different ways. A common use for glass is as an inert filler for polymerisable compositions, and in this case an inert glass is normally desirable and used. A second use for glasses in dentistry is the manufacture of crowns or inlays, and in this case it is essential that the glasses are not only inert, but also have a high surface hardness. It is also desirable for such glasses that they have a relatively low melting point so that formation of the crown or inlay is facilitated. Further examples of the use of glass in dental applications are in the so called "silicate" cements where an acid soluble glass is mixed with phosphoric acid, and "polyelectrolyte" cements where an acid soluble glass is mixed with a polyacid such as polyacrylic acid, polymaleic acid, polyvinyl phosphonate, or the like. This latter class of cements are often called glass-ionomer cements.

U.S. Pat. No. 4,814,362 discloses alkaline earth metal aluminofluorosilicate glasses suitable as ion-sources in dental glass ionomer compositions, whereby the glasses contain strontium in order to provide radioopacity. U.S. Pat. No. 5,318,929 discloses an apatite glass ceramic for a glass ionomer cement. U.S. Pat. No. 5,360,770 discloses a further glass composition for a dental glass ionomer cement. The glass compositions known from these references do not contain zinc oxide.

U.S. Pat. No. 6,355,585 discloses a glass powder for a dental glass ionomer cement compositions, wherein the bending strength and tensile strength are improved by a specific elongated shape of glass particles. The glass compositions do not contain zinc as an essential component.

A zinc containing aluminoborate glass composition for a dental glass ionomer cement is known from U.S. Pat. No. 4,336,153. Ternary aluminium-zinc-silicate glasses for the preparation of polyalkenoate glass ionomer dental cements are disclosed in Darling M.; Hill R.; Biomaterials 1994, 15(4), 299-306. However, the glass compositions disclosed therein do not contain any fluoride.

With the phosphate and polyelectrolyte cements the glass takes part in the setting reaction and is thereby partially dissolved. For these purposes the glass must not be inert, but must possess a suitable degree of acid solubility which allows partial dissolution of the glass and release of ions. Since the phosphate and polyelectrolyte cements mainly harden by crosslinking of the acids by ions released from the glass, it is obvious that the glasses therefore have to contain elements capable of being crosslinked by the acid. Monovalent ions such as $Na^+$ and $K^+$ are not capable of crosslinking the acids, but a wide range of multivalent ions can be used for this purpose. The composition of the glass, leading to a desired reactivity or inertness, therefore varies widely according to its intended purpose but common desirable feature for dental use is that the glass is opaque to X-rays. This enables a dentist to see a restoration with X-rays, and facilitates diagnosis of further caries, or allows the dentist to remove the restoration with minimal destruction of the remaining tooth substance. Radiopacity of glasses used for crowns and inlays is also important in case the crown or inlay is accidentally swallowed. It can therefore be seen that glasses intended for dental applications have to fulfil many exacting and varying specifications depending on their intended use.

Attempts to develop suitable glasses are described, for instance, in Journal of Dental Research June 1979 pages 1607-1619, or more recently in U.S. Pat. Nos. 4,814,362, 5,318,929, 5,360,770, and application US 2004/0079258 A1. The latter application is for an "Inert Dental Glass", and it is claimed that this inert glass has been developed by replacing strongly basic oxides such as CaO, BaO, SrO, MgO, ZnO, $Na_2O$, $K_2O$, $Li_2O$ etc. with weakly basic oxides such as those in the Scandium or Lanthanide series. However MgO and ZnO are variously referred to in the application as weakly basic and suitable for replacing CaO and BaO (abstract), or as strongly basic and needing replacement (paragraph 0034) in order to obtain a suitable inert glass, and it is therefore not clear to which category MgO and ZnO are supposed to belong. In paragraph [00346] of 0079258 A1 for instance it is specifically mentioned that it was found that, by replacing or partially replacing the strongly basic ions $Li^+$, $Na^+$, $K^+$, $Ca^+$, $Sr^{2+}$, $Ba^{2+}$, and $Zn^{2+}$ with weakly basic ions such as $Sc^{3+}$, $Y^{3+}$ $La^{3+}$ or $Ce^{3+}$ or other ions from the Lanthanide series, a glass was obtained which set significantly more slowly. Contrary to expectations from this, it is an aim of the present invention to develop a slow setting glass containing high levels of calcium, strontium and zinc ions. In particular, a glass with a high zinc content is desired. Zinc oxide has been widely used in dentistry, mainly in conjunction with phosphoric acid, polycarboxylic acids, or with eugenol. The zinc oxide forms complexes when mixed with these materials, and the resulting hard masses are useful as filling materials and cements. These zinc containing materials have proved over many years of clinical use to be particularly bland and beneficial to tooth substance, and this has been attributed to the presence of $Zn^{2+}$ ions. For use with acidic formulation, the zinc oxide has to, be specially treated in order to have a sufficiently slow reaction time, and it is therefore not expected that its addition to glass will, per se, result in a slow reacting glass in a polyalkenoate formulation. A disadvantage of materials based on zinc oxide alone is that these have very poor physical properties, having a low strength, high abrasion, high water solubility, and poor aesthetics due to very high opacity. These ZnO based materials are therefore restricted to use as temporary fillings or in protected and invisible positions such as a cement under a crown. Attempts have been made to combine ZnO powder directly into a polyalkenoate cement, for instance as described in Journal of Hard Tissue Biology (2003), 12(1), 17-24. It was concluded in this study that ZnO contributes to inhibit dentine demineralization without major changes to the mechanical properties of the cement. However, ZnO is highly opaque and its incorporation in a polyalkenoate cement would reduce the aesthetics considerably. Due to the two separate setting mechanisms in this mixture, handling and setting properties are also reduced. In addition to having possible beneficial effects on the tooth and surrounding tissue, zinc is highly opaque to X-rays and helps to provide the radioopacity required in a dental filling material. In general, glasses used in polyalkenoate cements are rather too reactive and need special treatment to reduce the reactivity and provide a long enough working and setting time. Such treatment to reduce the reactivity of glasses can include heat treatment, etching with acid, coating the glass with a film, or a combination of one or more of these methods, as is described for example in JP 1991-285510. Although this is effective, it is an extra step in production which can go wrong, and also costs time and money. In addition, the surface layer of the glass is altered by etching or coating, and this surface layer is liable to later mechanical loss or abrasion during further compounding steps or transport so that the treatment becomes less effective. Calcium, as an element naturally present in teeth is also an important component of a dental glass, and its presence has been shown to encourage the formation of hydroxy apatite. Calcium can in some circumstances be replaced by strontium.

SUMMARY OF THE INVENTION

It is therefore a problem of the present invention to provide reactive glasses containing high levels of ZnO, and optionally CaO and SrO, but which nevertheless provide a sufficiently long working time when produced with a mean particle size of 0.1 to 100 µm, in particular 0.5 to 10 µm, and used in a polyalkenoate formulation preferably without further treatment to reduce their reactivity. In addition, the set polyalkenoate cement obtained from such a glass has to have sufficiently high physical properties to allow its use in exposed positions as a permanent filling, and a sufficiently high opacity to X-rays. Such glasses can also be mixed with organic polymerisable materials, and the mixture hardened by polymerization of the organic matrix.

According to a first aspect, the present invention provides an aluminosilicate glass composition comprising:
(a) 10-35% by weight of silica;
(b) 10-35% by weight of alumina;
(c) 3-30% by weight of zinc oxide;
(d) 4-30% by weight $P_2O_5$; and
(e) 3-25% by weight of fluoride,
which contains at most 3% by weight of alkaline metals calculated as $M_2O$, wherein M is Li, Na, and/or K, and wherein
the weight ratio of the sum of zinc oxide and fluoride to $P_2O_6$ of from 0.8 to 3.0.

According to a second aspect, the present invention provides a particulate glass filler, characterized by a glass composition of the invention.

According to a third aspect, the present invention provides a dental restorative composition comprising the particulate glass filler of the invention.

According to a fourth aspect, the present invention provides a process for the preparation of a dental cement composition, which comprises the following steps:

(a) providing a component containing a polyacid;
(b) providing a component containing a particulate glass filler, characterized by a glass composition of the invention;
(c) mixing components of step (a) and (b) in the presence of water for preparing a hardenable dental cement composition.

According to a fifth aspect, the present invention provides a use of the glass composition of the invention for the preparation of a dental restorative composition.

DETAILED DESCRIPTION OF THE PREFERRED EMBODIMENTS

The present invention provides an alumosilicate glass composition. The composition contains silicon, aluminum, zinc, phosphorous and fluorine as essential elements. Silicon, aluminum, zinc and phosphorous are contained in the composition as oxides. The properties of a glass ionomer depends on many factors, but general trends can be seen between the composition of the glass and the glass ionomer properties. Since the trends are not necessarily linear and there are many interactions, trends should not be extrapolated too far from known points. A change of most components in a glass affects the degree of crosslinking in the glass, and therefore most compositional changes affect the reactivity in some way. The following trends are seen in multiple regression analysis of the glass and properties of the resulting glass ionomers.

Silica (calculated as $SiO_2$) is contained in the glass composition according to the invention in an amount of from 10-35% by weight. In a preferred embodiment, silica is contained in an amount of from 18-30% by weight. If the amount in the composition is below the range, the solubility and reactivity of the glass may be too high, and the resulting glass ionomer may have low strength. If the amount in the composition is above the range, the properties of the glass may be deteriorated, and the resulting glass ionomer again may tend to become too fast setting.

Alumina (calculated as $Al_2O_3$) is contained in the glass composition according to the invention in an amount of from 10-35% by weight. The composition may contain at least 15% by weight of alumina. In a preferred embodiment, alumina is contained in an amount of from 20-30% by weight. If the amount in the composition is below the range, the properties of the glass may be deteriorated, and the glass may become very reactive. If the amount in the composition is above the range, the properties of the glass may be deteriorated, and the glass ionomer may have low strength.

The weight ratio between silica and alumina is preferably in a range of from 1.2 to 0.8, more preferably in a range of from 1.15 to 1.0. If the ratio in the composition is below the range, the properties of the glass may be deteriorated, and the glass may become very reactive. If the ratio in the composition is above the range, the properties of the glass may be deteriorated, and the reactivity of the glass may become very high and difficult to regulate.

Zinc oxide (calculated as ZnO) is contained in the glass composition according to the invention in an amount of from 3-30% by weight. In a preferred embodiment, zinc oxide is contained in an amount of from 3 to 25% by weight. If the amount in the composition is below the range, the properties of the glass may be deteriorated, and the rate of release of zinc ions from the glass ionomer will decrease. If the amount in the composition is above the range, the properties of the glass may be deteriorated, and the glass may tend to become too reactive.

Phosphorous (calculated as $P_2O_5$) is contained in the glass composition according to the invention in an amount of from 4-30% by weight. In a preferred embodiment, phosphorous is contained in an amount of from 8 to 20% by weight. Phosphorous atoms may be contained in the composition in the form of a phosphate. If the amount of phosphate in the composition is outside this range, then the working time and setting time may be deteriorated.

Fluoride is contained in the glass composition according to the invention in an amount of from 3-25% by weight. The glass composition may contain at least 5% by weight of fluoride. In a preferred embodiment, fluoride is contained in an amount of from 6-16% by weight. If the amount in the composition is below the range, the properties of the glass may be deteriorated. The glass may become less reactive and the strength of a glass ionomer made from it may be reduced. If the amount in the composition is above the range, the properties of the glass are deteriorated. The glass may become highly reactive and more difficult to use in a glass ionomer formulation.

Besides the essential elements, the glass composition of the present invention may further comprise up to 30% by weight of calcium oxide and/or strontium oxide. Preferably, the composition contains 5 to 25% by weight or about 15 to 25% by weight of calcium oxide and/or strontium oxide.

The glass composition preferably does essentially not contain any alkaline metals. In particular, the composition contains at most 3% by weight, preferably at most 1.5% by weight, of alkaline metals $M_2O$, wherein M is Li, Na, or K. The glass composition may contain at most 2% by weight of alkaline metals calculated as $M_2O$, wherein M is Li, Na, and/or K. If the content of alkaline metals in the composition is above this range, the glass may become more soluble and the working time and the setting time of a corresponding ionomer cement may be deteriorated.

The glass composition preferably does essentially not contain any boron atoms. In particular, the composition contains at most 2% by weight, preferably at most 1.5% by weight, of $B_2O_3$. If the content of $B_2O_3$ in the composition is above this range, the hydrolytic stability of a corresponding cement may be deteriorated.

In a further embodiment, the alumosilicate glass composition is essentially free of zirconium. In particular, the composition contains less than 2% by weight, preferably at most 1.5% by weight, of $ZrO_2$.

In a preferred embodiment, the glass composition is characterized by a weight ratio of zinc oxide to $P_2O_5$ of from 2.0 to 0.2. If the weight ratio is outside this range, the working time and the setting time of a corresponding ionomer cement may be deteriorated.

The glass composition is characterized by a weight ratio of the sum of zinc oxide and fluoride to $P_2O_5$ of from 0.8 to 3.0. Preferably, the weight ratio of the sum of zinc oxide and fluoride to $P_2O_5$ is at most 2.0. If the weight ratio is outside this range, the working time and the setting time of a corresponding ionomer cement may be deteriorated.

In a preferred embodiment, the present invention provides an alumosilicate glass composition comprising:
(a) 10-35% by weight of silica;
(b) 10-35% by weight of alumina;
(c) 3-30% by weight of zinc oxide;
(d) 4-30% by weight $P_2O_5$; and
(e) 5-25% by weight of fluoride,
which contains at most 2% by weight of alkaline metals calculated as $M_2O$, wherein M is Li, Na, and/or K, and wherein
the weight ratio of the sum of zinc oxide and fluoride to $P_2O_5$ of from 0.8 to 3.0.

In an especially preferred embodiment, the aluminosilicate glass composition comprising:
(a) 20-26% by weight of silica;
(b) 21-27% by weight of alumina;
(c) 15-21% by weight of zinc oxide;
(d) 15-21% by weight $P_2O_5$; and
(e) 6-10% by weight of fluoride,
and 11-17% by weight of CaO.

The alumosilicate glass composition of the invention may be prepared according to any method for preparing a dental glass. In particular, it is possible to prepare a mixture of suitable starting materials. Accordingly, the mixture may typically contain silica, aluminium oxide, phosphorous pentoxide, and a suitable fluoride source such as aluminum trifluoride. Optionally, the mixture may contain calcium or strontium carbonate or the corresponding fluorides. Advantageously, the mixture is subsequently shaken to thoroughly mix the components together. Subsequently, in a preferred method, the mixture may be heated at a suitable rate of 50 to 300° C./min to a first elevated temperature of about 600 to 800° C. to allow degassing and moisture loss. After a suitable amount of time at the elevated temperature, the mixture is heated at a suitable rate of 50 to 300° C./min to a second elevated temperature of about 1300 to 1500° C. and held at this temperature for about 60 to 180 minutes, then the temperature is increased at a suitable rate of 50 to 300° C./min to a third elevated temperature of from 1400 to 1600° C. and held at this temperature for about 10 to 60 minutes. After withdrawing the crucible from the oven, the molten glass is poured directly into cold water to give broken glass fragments.

The glass fragments may then be milled, for example in a dry ball mill, to give a powder with a mean particle size in a range of less than 100 µm, preferably less than 10 µm. This powder may then be further milled, for example in water slurry, to give glass powder with an even smaller mean particle size, typically in the range of from 0.1 to 8 µm. Particle size measurements may be made by any conventional method such as embodied by a Malvern Particle Master Sizer model S. Because the reactivity of the glass particles depends an their size and surface area, it is important that particle size is carefully controlled. The glass may also be prepared by other methods, including alternative heating and cooling procedures or a sol-gel process.

The glass composition of the invention may be used for the preparation of a dental restorative composition. Accordingly, the present invention also provides a particulate glass filler characterized by the glass composition according to the first aspect of the invention. Preferably, the particulate glass filler has an average particle size in the range of from 0.1 to 100 µm, more preferably in the range of from 1.0 to 10 µm.

The particulate glass filler may be incorporated into a dental restorative composition. A suitable dental restorative composition is an glass-ionomer cement. The glasses of the invention are suitable for use as ion-sources in glass ionomer cement compositions. The invention further provides a method of producing a cross-linked glass ionomer cement which comprises reacting in the presence of water a polymer containing free acidic groups such as carboxyl groups with the particulate glass of the invention. Accordingly, the dental restorative composition preferably further comprises an acid or a polyacid. The polyacid may comprise any mixture of suitable acidic groups, including carboxylic, phosphoroc, phosphonic, sulfonic, boric and the like, which may be attached either directly to the polymer chain or via linking groups such as ester, amide, anhydride, ether, amine, urethane, or a hydrocarbyl chain. A suitable polyacidic polymer containing free carboxyl groups is preferably a homopolymer of acrylic acid. Copolymers of acrylic acid with one or more other ethylenically unsaturated carboxylic acids such as maleic, itaconic acid or methacrylic acid, may be employed. The acrylic acid polymer or copolymer suitably has a mean molecular weight of from 5000, in particular 10000 to 150000, preferably from 35000 to 70000, most preferably from preferably 45000 to 75000. In a preferred embodiment, the dental restorative composition further comprises at least one ethenically unsaturated compound.

The weight ratio of polyacid to glass is suitably from 0.1:1 to 0.5:1, preferably 0.2:1 to 0.4:1; and the weight ratio of water to glass is preferably 0.4:1 to 0.1:1.

The reaction of the polyacrylic acid and glass may be carried out in the presence of other materials serving to alter or modify the working time and/or setting time of the mixture, e.g. a hydroxycarboxylic acid such as tartaric acid serving to increase the rate of set of the composition.

Compositions for forming a cement from the glass of the invention and polyacid may be provided as two-part packs, one part comprising an aqueous solution of the polyacrylic acid (and optionally working/setting time modifiers) and the other part comprising a particulate glass. Alternatively, a dry blend may be formed of particulate glass and a powdered polymer for subsequent addition of water to form a cement-forming composition. In this latter case working/setting time modifiers may be present in the dry blend or in the water. In a further alternative one part comprising an aqueous solution of the polyacrylic acid (and optionally working/setting time modifiers) and the other part comprising a dry blend may be formed of particulate glass and a powdered polymer may be provided to form a cement-forming composition.

The glasses of the invention may also be used in a radically polymerisable dental composition. Accordingly, the invention provides a composition, comprising a polymerisable composition containing the glass of the invention as a filler. Such a composition may be a composite dental restorative material, i.e. some derived from the polymerization of a composition comprising one or more ethylenically unsaturated monomers, a particular filler and a polymerization initiator for the ethylenically unsaturated monomer(s) which typically comprise acrylate monomers, that is esters of acrylic or methacrylic acid.

According to the present invention, the process for the preparation of a dental cement composition comprises the following steps:
(a) providing a component containing a polyacid;
(b) providing a component containing a particulate glass filler according to the invention;
(c) mixing components of step (a) and (b) in the presence of water for preparing a hardenable dental cement composition.

In order that the invention may be well understood the following Examples are given by way of example only. In the Examples all percentages are by weight unless otherwise stated.

Experimental Part

Glasses with the compositions given in the table were either obtained from commercial sources, or were smelted in an electrical furnace at 1400 to 1500° C. The procedure for smelting one glass (example 1) is given below, and other glasses not obtained commercially were made analogously using appropriate ingredients.

EXAMPLE 1

The following materials by weight were added together. Silica (25.8 parts), aluminium oxide (23.4 parts), calcium carbonate (25.0 parts), phosphorous pentoxide (16.4, parts), and calcium fluoride (20.4 parts). The mixture was placed in a glass bottle and tumbled for one hour to thoroughly mix the components together. The mixture was then transferred to an aluminium oxide crucible and heated at a rate of 200° C./min to 700° C. to allow degassing and moisture loss. After ten minutes at 700° C. the mixture was heated at 200° C./min to 1400° C. and held at this temperature for 120 minutes, then the temperature was increased at 200° C./min to 1500° C. and held at this temperature for 30 minutes. The oven was then opened, the crucible was withdrawn, and the molten glass was poured directly into cold water to give broken glass fragments.

Reduction of Particle Size

The glass, whether smelted as above or obtained commercially, was first milled if necessary in a dry ball mill to give powder with a mean particle size under about 10 μm. This powder was then further milled in water slurry to give glass powder with a mean particle size of approximately 3 μm. A portion of this glass was further milled to give glass powder with a mean particle size of approximately 1 μm. Particle size measurements were made an a Malvern Particle Master Sizer model S. Because the reactivity of the glass particles depends an their size and surface area, it is important that particle size is careful controlled.

Standard Test Methods

Standard Test Method 1

The glass powder with mean size of 3 μm (86.64 parts) was mixed with dried polyacrylic acid (12.27 parts) and finely ground tartaric acid (1.09 parts). The components were tumbled together in a glass bottle for one hour to give a homogenous mixture. This powder mixture was investigated by combining three parts by weight of the powder with 1 part by weight of 40% solution of polyacrylic acid in water at 23° C.

Standard Test Method 2

The glass powder (1.65 parts by weight) was combined at 23° C. with 1 part by weight of an aqueous solution containing 40% polyacrylic acid and 12% tartaric acid, and the two were spatulated together until a homogenous paste was obtained.

For both test methods the working time (w.t.) was taken as the time from the start of mixing to the time when the mixture became rubber like and unusable. The setting time (s.t.) and compressive strengths were determined according to ISO 9917-1.

TABLE 1

| reference | Example | $SiO_2$ | $Al_2O_3$ | CaO | ZnO | $P_2O_5$ | $CaF_2$ | F | w.t. minutes | s.t. minutes |
|---|---|---|---|---|---|---|---|---|---|---|
| 9-34-7 | 1 | 25.8 | 23.4 | 14 | 0.0 | 16.4 | 20.4 | 9.9 | 1.83 | 3.33 |
| 9-50-2 | 2 | 25.7 | 23.3 | 10.4 | 4 | 16.3 | 20.3 | 9.9 | 1.66 | 4.66 |
| 9-67-2 | 3 | 25.7 | 19.4 | 10.5 | 8 | 16.4 | 20.4 | 9.91 | 1 | 3.83 |
| 9-85-2 | 4 | 26 | 22.0 | 10.0 | 8.0 | 22 | 12 | 5.84 | 2.67 | 21.33 |

It is conventional to express the composition of a glass in terms of the elements calculated as their oxides. In table 2 the examples 1 to 4 are shown in this way with the addition of four commercial glasses.

TABLE 2

| reference | Example | SiO$_2$ | Al$_2$O$_3$ | CaO | SrO | ZnO | P$_2$O$_5$ | Na$_2$O | F$^-$ | w.t. minutes | s.t. minutes |
|---|---|---|---|---|---|---|---|---|---|---|---|
| 9-34-7 | 1 | 24.8 | 22.5 | 27.5 | 0.0 | 0.0 | 15.7 | 0.0 | 9.5 | 1.83 | 3.33 |
| 9-50-2 | 2 | 24.7 | 22.4 | 24.0 | 0.0 | 3.8 | 15.6 | 0.0 | 9.5 | 1.66 | 4.66 |
| 9-67-2 | 3 | 24.6 | 18.6 | 24.0 | 0.0 | 7.6 | 15.7 | 0 | 9.5 | 1.00 | 3.83 |
| 9-85-2 | 4 | 25.4 | 21.5 | 18.2 | 0 | 7.8 | 21.5 | 0 | 5.7 | 2.67 | 21.33 |
| 018-190* | 5 | 30 | 20 | 0 | 0 | 10 | 0 | 0 | 20 | 0.42 | — |
| DF3§ | 6 | 37 | 17 | 14 | 0 | 22 | 0 | 4.2 | 6 | 0.2 | — |
| Chemfil | 7 | 27.8 | 31.3 | 10.8 | 0 | 0 | 7 | 10.6 | 14.8 | 0.67 | — |
| ChemFlex | 8 | 32.1 | 24.6 | 0 | 28.7 | 0 | 4.8 | 2.9 | 12.3 | 0.5 | — |

*commercially available from Schott, Germany;
§commercially available from John Kent Ltd. England.
ChemFil and ChemFlex are commercial products of Dentsply.
w.t. and s.t. in examples 1 to 4 shown in tables 1 and 2 are based on standard test method 1.

From examples 1 and 2 it is seen that decreasing the CaO content of the glass and adding ~4% ZnO leads to a slightly shorter working time, meaning that the glass became more reactive. In example 3 the ZnO content was increased to ~7.6% while the CaO content was held constant, and this led to a further shortening of working time to 1 minute, meaning a ZnO content of ~8%. In example 4 the setting time of the polyalkenoate cement has increased to over 21 minutes however, so that further adjustments of the composition are needed to obtain a suitable setting time. It is also apparent from the above that the reactivity of a glass and the working time of a polyalkenoate cement produced from it depends on many factors, and does not depend on one component alone.

Further glass compositions were therefore smelted as described for example 1, and their compositions are given in table 3, calculated as the oxides.

TABLE 3

| Example | SiO$_2$ | Al$_2$O$_3$ | CaO | SrO | ZnO | P$_2$O$_5$ | Na$_2$O | F | w.t. minutes | s.t. minutes | radio-opcity |
|---|---|---|---|---|---|---|---|---|---|---|---|
| 9 | 24.7 | 22.5 | 20.3 | 0 | 7.7 | 15.4 | 0 | 9.5 | 3.25 | 3.50 | |
| 10 | 24.8 | 22 | 15.8 | 0 | 13.4 | 13.4 | 0 | 10.7 | 2.21 | 2.75 | |
| 11 | 20.4 | 20.4 | 26.0 | 0 | 9.7 | 16.5 | 0 | 7.1 | 2.59 | 3.00 | |
| 12 | 23.1 | 22.2 | 0.0 | 0.0 | 17.4 | 16.4 | 0 | 8.4 | 2.37 | 2.92 | 1.6 |
| 13 | 23.1 | 22.2 | 12.5 | 0.0 | 17.4 | 16.4 | 0 | 8.4 | 1.91 | 2.25 | |
| 14 | 22.2 | 21.2 | 12.5 | 0.0 | 21.2 | 14.5 | 0 | 8.4 | 1.92 | 2.42 | 1.5 |
| 15 | 22.5 | 21.6 | 8.8 | 6.2 | 16.9 | 15.9 | 0 | 8.2 | 1.75 | 2.92 | 1.7 |
| 16 | 21.8 | 20.9 | 5.0 | 12.4 | 16.4 | 15.5 | 0 | 7.9 | 1.75 | 2.66 | 2.3 |
| 17 | 26.0 | 22.8 | 4.4 | 13.6 | 12.1 | 13.5 | 2.8 | 4.8 | 0.9 | 0.9 | | w.t. and s.t. in the examples shown in tables 1 and 2 are based on Test method 2.

that the glass became even more reactive. In further examples 5 and 6, the glass 018-090 commercially available from Schott has a ZnO content of 10%, no phosphate, and a very high fluorine content. This glass had a working time of only 25 seconds and the setting time was too short to measure when tested under the conditions described earlier. This glass would therefore need special treatment in order to reduce its reactivity. Similarly the glass DF3 obtainable commercially from John Kent, England, containing 22% ZnO and also 4.2% sodium oxide had a working time under these test conditions of only 12 seconds and the setting time was also too short to measure. Similarly, the glasses of examples 7 and 8 are also too reactive when used without pre-treatment. Although these commercially available glasses undoubtedly provide a suitable working and setting time after appropriate treatment, one specific aim of this invention is to provide glasses which preferably may be used without such treatment. From the results above, adding ZnO to the glass seems to lead to a more reactive glass, and it is counter-intuitive to expect that a less reactive glass could be obtained even when a high ZnO content is used. However example 4 indicates that increasing the phosphate and reducing the fluoride contents of the glass results in a longer working time of the glass-polyalkenoate mixture even with

The invention claimed is:

1. A dental glass ionomer cement composition comprising:
   (i) an acid or a polyacid; and
   (ii) a particulate reactive aluminosilicate glass composition having a mean particle size in the range of 0.1 to 100 μm, the particulate reactive aluminosilicate glass composition comprising:
      (a) 18-30% by weight of silica;
      (b) 20-30% by weight of alumina;
      (c) 3-25% by weight of zinc oxide;
      (d) 8-20% by weight P$_2$O$_5$;
      (e) 5-26% by weight calcium oxide and/or strontium oxide; and
      (f) 6-16% by weight of fluoride,
   wherein the particulate reactive aluminosilicate glass composition is free of Li$_2$O, Na$_2$O, and K$_2$O;
   wherein the weight ratio of the sum of zinc oxide and fluoride to P$_2$O$_5$ is in the range of 0.8 to 3.0; and
   wherein the weight ratio between silica and alumina is in the range of 1.2 to 0.8.

2. The dental glass ionomer cement composition according to claim 1, wherein the particulate reactive aluminosilicate glass composition comprises 15 to 25% by weight of calcium oxide and/or strontium oxide.

3. The dental glass ionomer cement composition according to claim 1, wherein the particulate reactive aluminosilicate glass composition has a weight ratio of zinc oxide to $P_2O_5$ in the range of 2.0 to 0.2.

4. The dental glass ionomer cement composition according to claim 1 further comprising a hydroxycarboxylic acid, and comprising the polyacid.

5. The dental glass ionomer cement composition according to claim 4, which further comprises at least one ethylenically unsaturated compound.

6. A process for the preparation of a dental glass ionomer cement composition, which comprises the following steps:
(a) providing a component containing a polyacid;
(b) providing a component containing a particulate reactive aluminosilicate glass composition having a mean particle size in the range of 0.1 to 100 μm, the particulate reactive aluminosilicate glass composition comprising:
18-30% by weight of silica;
20-30% by weight of alumina;
3-25% by weight of zinc oxide;
8-20% by weight $P_2O_5$;
5-26% by weight calcium oxide and/or strontium oxide; and
6-16% by weight of fluoride,
wherein the particulate reactive aluminosilicate glass composition is free of $Li_2O$, $Na_2O$, and $K_2O$;
wherein the weight ratio of the sum of zinc oxide and fluoride to $P_2O_5$ is in the range of 0.8 to 3.0; and
wherein the weight ratio between silica and alumina is in the range of 0.8 to 1.2; and
(c) mixing components of step (a) and (b) in the presence of water for preparing a hardenable dental cement composition;
wherein the process does not include a treatment to reduce a reactivity of the glass composition.

7. The dental glass ionomer cement composition according to claim 1, which is free of zirconium.

8. The dental glass ionomer cement composition according to claim 1, which does not contain any boron.

9. The dental glass ionomer cement composition of claim 1 comprising the polyacid; and further comprising water; wherein the weight ratio of the polyacid to the glass is 0.1:1 to 0.5:1.

10. The dental glass ionomer cement composition according to claim 9, wherein the weight ratio of water to the glass is 0.4:1 to 0.1:1.

11. The dental glass ionomer cement composition according to claim 10, further comprising a hydroxycarboxylic acid.

12. The process according to claim 6, wherein the particulate reactive aluminosilicate glass composition is prepared by:
heating a mixture of the silica, the alumina, the zinc oxide, the $P_2O_5$, the calcium oxide and/or strontium oxide, and the fluoride to a first elevated temperature of about 600 to 800° C.;
heating the mixture to a second elevated temperature of about 1300 to 1500° C.;
maintaining the mixture at the second elevated temperature for about 60 to 80 minutes;
heating the mixture to a third elevated temperature of 1400 to 1600° C.;
maintaining the mixture at the third elevated temperature for 10 to 60 minutes;
quenching the molten mixture to give broken glass fragments; and
milling the broken glass fragments to form the particulate reactive aluminosilicate glass composition.

13. The dental glass ionomer cement composition according to claim 1, wherein the particulate reactive aluminosilicate glass composition comprises:
(i) 20.4-24.8% by wt silica;
(ii) 20.4-22.5% by wt alumina;
(iii) 7.7-21.2% by wt zinc oxide;
(iv) 13.4-16.5% by wt $P_2O_5$;
(v) 12.5-26% by wt calcium oxide and/or strontium oxide; and
(vi) 7.1-10.7% by wt fluoride.

14. The dental glass ionomer cement composition according to claim 13, wherein
a weight ratio of zinc oxide to $P_2O_5$ is the range of 2.0 to 0.2.

15. The dental glass ionomer cement composition according to claim 4, wherein the hydroxycarboxylic acid comprises tartaric acid, the polyacid comprises polyacrylic acid, and the dental glass ionomer cement composition at 23° C. has a working time in a range of about 1.75 to 3.25 minutes and a setting time in a range of about 2.25 to 3.5 minutes without a treatment to reduce a reactivity of the particulate reactive aluminosilicate glass composition.

16. The dental glass ionomer cement composition according to claim 1, wherein the particulate reactive aluminosilicate glass composition does not contain any alkali metals.

17. The dental glass ionomer cement composition according to claim 15, wherein the glass ionomer cement restorative composition comprises 1.65 parts by weight of the particulate reactive aluminosilicate glass composition and 1 part by weight of an aqueous solution comprising 40% polyacrylic acid and 12% tartaric acid.

18. The dental glass ionomer cement composition according to claim 13, wherein the particulate reactive aluminosilicate glass composition is selected such that the dental glass ionomer cement composition at 23° C. comprising 1.65 parts by weight of the particulate reactive aluminosilicate glass composition and 1 part by weight of an aqueous solution comprising 40% polyacrylic acid and 12% tartaric acid has a working time in a range of about 1.75 to 3.25 minutes and a setting time in a range of about 2.25 to 3.5 minutes without a treatment to reduce a reactivity of the particulate reactive aluminosilicate glass composition.

* * * * *